United States Patent
Chase

(10) Patent No.: US 11,583,285 B2
(45) Date of Patent: Feb. 21, 2023

(54) BLEEDING CONTROL DEVICE

(71) Applicant: William Chase, Avon, CT (US)

(72) Inventor: William Chase, Avon, CT (US)

( * ) Notice: Subject to any disclaimer, the term of this patent is extended or adjusted under 35 U.S.C. 154(b) by 258 days.

(21) Appl. No.: 16/867,798

(22) Filed: May 6, 2020

(65) Prior Publication Data
US 2020/0281601 A1    Sep. 10, 2020

Related U.S. Application Data

(62) Division of application No. 16/733,655, filed on Jan. 3, 2020, now Pat. No. 11,259,813.

(60) Provisional application No. 62/815,632, filed on Mar. 8, 2019.

(51) Int. Cl.
*A61B 17/12* (2006.01)
*A61B 17/00* (2006.01)

(52) U.S. Cl.
CPC .... *A61B 17/12136* (2013.01); *A61B 17/1204* (2013.01); *A61B 2017/00548* (2013.01); *A61B 2017/12004* (2013.01)

(58) Field of Classification Search
CPC ........ A61B 17/12022; A61B 17/12027; A61B 17/12031; A61B 17/1204; A61B 17/12136; A61B 2017/00548; A61B 2017/12004; A61B 2017/1205; A61B 2017/12054
See application file for complete search history.

(56) References Cited

U.S. PATENT DOCUMENTS

| 4,944,726 A | 7/1990 | Hilal et al. |
| 2004/0127931 A1 | 7/2004 | Kincaid et al. |
| 2004/0254625 A1 | 12/2004 | Stephens et al. |
| 2005/0143689 A1 | 6/2005 | Ramsey, III |
| 2008/0119785 A1 | 5/2008 | Ramsey et al. |
| 2009/0149870 A1* | 6/2009 | Jugenheimer ...... A61B 17/1227 606/139 |
| 2010/0198249 A1 | 8/2010 | Sabliere |
| 2011/0270225 A1 | 11/2011 | Ehrenreich et al. |

(Continued)

FOREIGN PATENT DOCUMENTS

WO    2019246443 A1    12/2019

OTHER PUBLICATIONS

International Search Report for corresponding PCT Application No. PCT/US2020/012159 dated Feb. 18, 2020.

(Continued)

*Primary Examiner* — Tuan V Nguyen
(74) *Attorney, Agent, or Firm* — McCormick, Paulding & Huber PLLC

(57) ABSTRACT

A bleeding control device for mitigating bleeding includes an outer storage container housing, a compressed gas canister, wound blocking contents and a control element. The bleeding control device may be used to deliver variable contents to a wound at the site of injury to control the bleeding of a victim as temporary solution for mitigating the bleeding until more advanced medical care can be provided. A bleeding control device includes a canister housing, a compressed gas canister arranged within the canister housing, a tube connected to the canister housing, an inflatable balloon disposed on the tube, the inflatable balloon being fluidly connected to the compressed gas canister, and a control element configured to activate the compressed gas canister to inflate the inflatable balloon.

15 Claims, 5 Drawing Sheets

(56) References Cited

U.S. PATENT DOCUMENTS

| | | |
|---|---|---|
| 2012/0209317 A1* | 8/2012 | Oepen ................ A61B 17/0644 |
| | | 606/213 |
| 2014/0163467 A1 | 6/2014 | Ramsey, III et al. |
| 2014/0207201 A1 | 7/2014 | Piha et al. |
| 2015/0142045 A1 | 5/2015 | Bacich |
| 2016/0058988 A1 | 3/2016 | Kesten et al. |
| 2018/0071492 A1 | 3/2018 | Laby et al. |
| 2018/0125690 A1 | 5/2018 | Brister et al. |
| 2018/0303499 A1 | 10/2018 | Bonneau et al. |

OTHER PUBLICATIONS

International Search Report for PCT/US2020/012159 dated Apr. 1, 2020.

\* cited by examiner

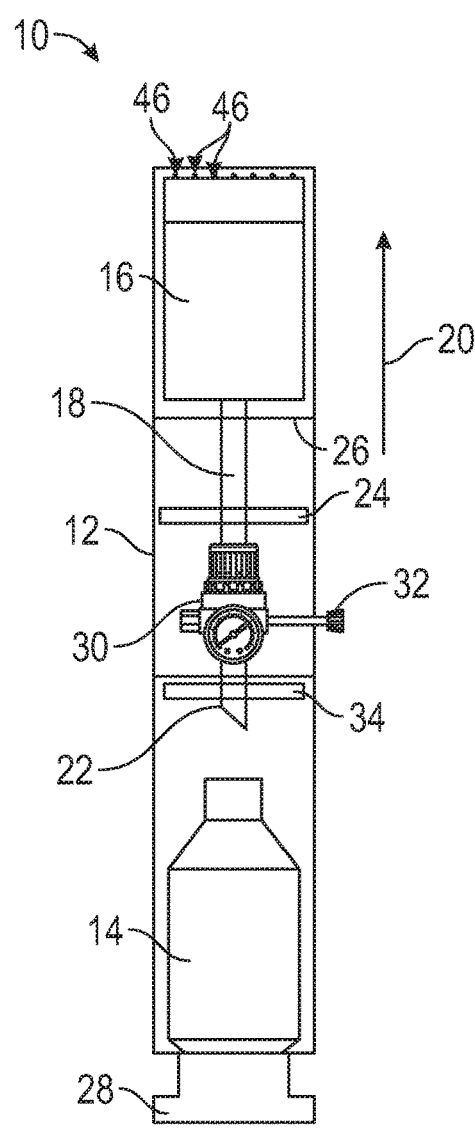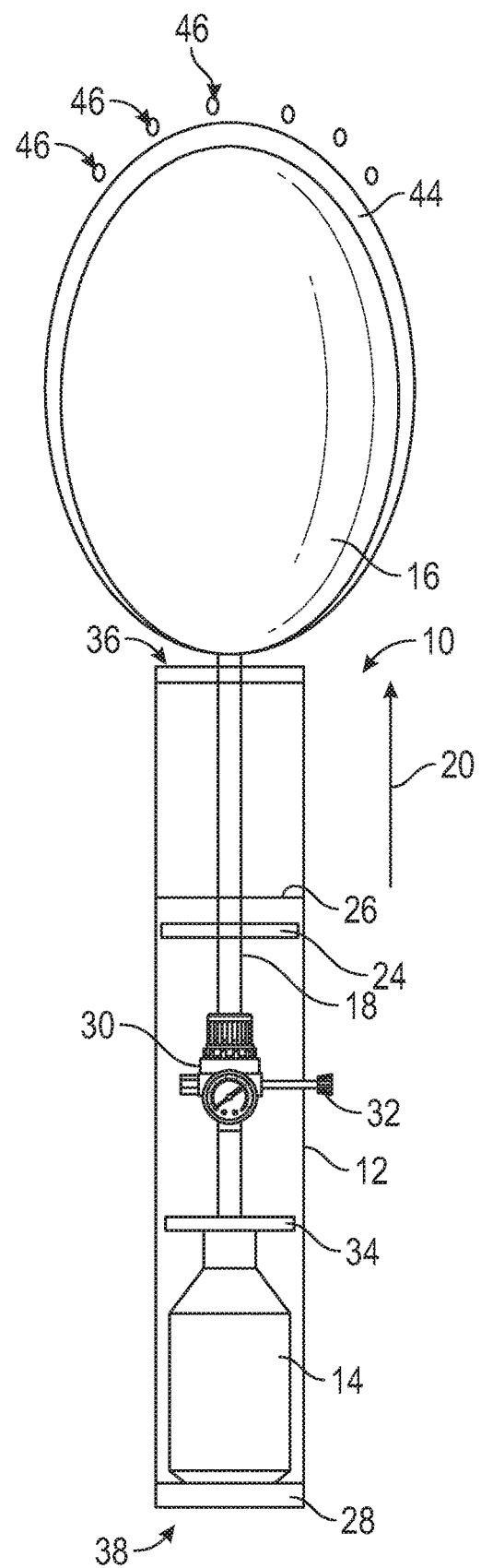
FIG. 1
FIG. 2

BLEEDING CONTROL DEVICE

CROSS-REFERENCE TO RELATED APPLICATIONS

This application is a divisional of U.S. patent application Ser. No. 16/733,655, filed on Jan. 3, 2020, which claims the benefit of U.S. Provisional Patent Application No. 62/815,632, filed on Mar. 8, 2019, each of which is incorporated herein by reference in its entirety.

TECHNICAL FIELD

The present disclosure generally relates to bleeding control at or near the site of an injury at the time when traumatic injury occurs, and more particularly, to an apparatus and method for quickly and efficiently covering and blocking a wound to control bleeding without needing advanced knowledge of first aid procedures.

BACKGROUND

Current bleeding control techniques for rapid blood loss include applying a tourniquet above a bleeding injury and/or packing a wound with gauze and applying pressure to the wound to reduce bleeding. In either case, if pressure is reduced, even for a short duration, any clots that have formed to slow bleeding may become ruptured and dislodged, causing bleeding to resume at a flow level comparable to the bleeding prior to treatment being applied. Additionally, typical wound packing must be done at a given density, generally immediately following the injury, otherwise the blood flow may not be slowed to an acceptable level. Moreover, some first aid training must have been acquired for effective use of such prior art techniques, or treatment may not extend the very short duration between untreated bleeding wounds and death. Accordingly, there is a need for a device that can be deployed with minimal effort to assist in such situations and assist in controlling and mitigating bleeding, that is, moreover, portable and easy enough to use in trauma situations by a layperson.

SUMMARY

In embodiments according to the present disclosure a bleeding control device includes an outer storage container housing, a compressed gas canister arranged within the outer storage container housing, wound blocking content arranged within the outer storage container housing, and an input element configured to activate the compressed gas canister to deploy the wound blocking content from the outer storage container housing.

In embodiments according to the present disclosure a bleeding control device includes an outer storage container housing, a compressed spring arranged within the outer storage container housing, wound blocking content arranged within the outer storage container housing, and an input element configured to activate the compressed spring to deploy the wound blocking content from the outer storage container housing.

In embodiments according to the present disclosure a bleeding control device includes a canister housing, a compressed gas canister arranged within the canister housing, a tube connected to the canister housing, an inflatable balloon disposed on the tube, the inflatable balloon being fluidly connected to the compressed gas canister, and an input element configured to activate the compressed gas canister to inflate the inflatable balloon.

Objects, features and advantages of the present invention will become apparent in light of the description of embodiments and features thereof, as enhanced by the accompanying figures.

BRIEF DESCRIPTION OF THE DRAWINGS

FIG. 1 is an illustration of a bleeding control device in a non-deployed state in accordance with the present disclosure;

FIG. 2 is an illustration of the bleeding control device of FIG. 1 in a deployed state in accordance with the present disclosure;

DETAILED DESCRIPTION

Figure 3:
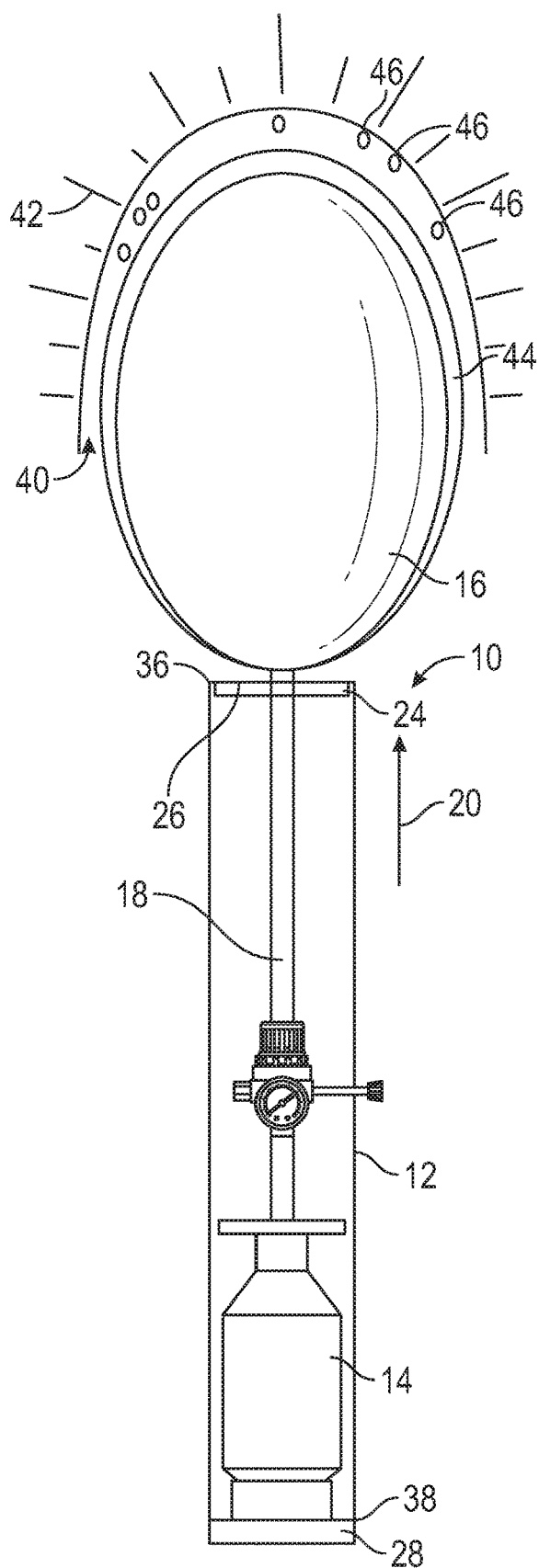
FIG. 3 is an illustration of a variant embodiment of the bleeding control device of FIG. 1 in a deployed state in a wound of a patient in accordance with the present disclosure.

Referring to FIG. 1, a schematic illustration of a bleeding control device 10 is shown in a non-deployed state in accordance with the present disclosure. The device 10 comprises an outer storage container housing 12, a compressed gas canister 14, wound blocking content(s) 16 and a gas supply line 18 connected to the wound blocking contents 16. The outer storage container housing 12 has a tubular-shaped body that extends in a longitudinal direction 20 from a proximate end 38 to a distal end 36. The compressed gas canister 14 is disposed within the outer storage container housing 12 proximate the proximate end 38 and the wound blocking contents 16 is disposed within the outer storage container housing 12 proximate the distal end 36. The gas supply line 18 extends in the longitudinal direction 20 within the outer storage container housing 12 from the wound blocking contents 16 to a piercing end 22 proximate to the compressed gas canister 14. A piston 24 is arranged within the outer storage container housing 12 between the compressed gas canister 14 and the wound blocking contents 16, with the gas supply line 18 extending through the piston 24. The piston 24 is movable along the gas supply line 18 in the longitudinal direction 20 and is configured to drive the wound blocking contents 16 from the device 10. The device 10 further comprises an activator 28 configured to activate the compressed gas canister 14 and/or actuate the compressed the gas canister 14. The activator 28 may be, for example, a mechanism that pierces the gas canister 14 to release the compressed gas, a controllable valve that is opened through a user input such as a button, switch or the like to release the compressed gas, or any other known mechanism for controlling the flow of gas from a reservoir. In the embodiment shown in FIG. 1, the wound blocking contents 16 is an inflatable balloon that is configured to be inflated by compressed gas from the compressed gas canister 14 when the compressed gas canister 14 is activated by the activator 28. The bleeding control device 10 may be configured to output gas flow from the compressed gas canister 14 at a fixed preset pressure level to inflate the inflatable balloon to the fixed pressure level.

The bleeding control device 10 may optionally comprise a regulator 30 configured to control the output gas flow from the compressed gas canister 14 when activated. The flow through the regulator 30 may be variably controlled and/or set to a desired pressure output through an adjustable control 32. When the optional regulator 30 is included, the inflatable balloon 16 may be inflated to a desired or predetermined pressure (and maintain that pressure) as is discussed in greater detail below. In some embodiments, the regulator 30 may be connected directly or indirectly with the compressed gas canister 14, and an input element, such as the activator 28 or the adjustable control 32, is configured to cause the regulator 30 to activate the compressed gas canister 14 by causing the regulator 30 to open the compressed gas canister 14 without the need to pierce the compressed gas canister 14. For example, the regulator 30 may be in the form of a valve that determines an opening degree of the compressed gas canister 14.

As seen in FIG. 1, the bleeding control device 10 may also comprise an optional stop 34 that prevents the piston 24 and/or wound blocking contents 16 from being introduced too far into the bleeding control device 10.

Referring to FIG. 2, a schematic illustration of the bleeding control device 10 of FIG. 1 is shown in a deployed state. To change the bleeding control device 10 from the non-deployed state shown in FIG. 1 to the deployed state of FIG. 2, the activator 28 is actuated by a user. In this embodiment, the activator 28 is actuated by pressing the activator 28 into the interior of the outer storage container housing 12 at the proximate end 38 towards the compressed gas canister 14. This pushes the compressed gas canister 14 against the piercing end 22 of the gas supply line 18, which pierces the compressed gas canister 14 and causes pressurized gas to flow into the inside of the outer storage container housing 12. This flow of pressurized gas may also be accomplished with a valve instead of a piercing connection to the canister 14. The pressurized gas flows throughout the outer storage container housing 12, both outside the gas supply line 18 and within the gas supply line 18. The pressurized gas outside of the gas supply line 18 causes the piston 24 is to move in the longitudinal direction 20 toward the distal end 36 of the outer storage container housing 12, which drives the piston 24 in the longitudinal direction 20 toward the distal end 36. The movement of the piston 24 pushes the inflatable balloon 16 (wound blocking content(s)) out of the outer storage container housing 12 at the distal end 36 through physically pushing with direct or indirect contact with the inflatable balloon 16 (or wound blocking content(s)) and/or through causing the air between the piston 24 and the inflatable balloon 16 to push the inflatable balloon 16. When the piston 24 finishes its travel and/or reaches the piston stop 26, the piston 24 stops moving and the pressurized gas inside the gas supply line 18 inflates the inflatable balloon 16 outside of the outer storage container housing 12. Optionally, once the piston 24 reaches the intended travel distance the gas flow outside the gas supply line may cease. In this embodiment, the piston stop 26 is arranged at an intermediate position of the device 10 in the longitudinal direction 20, but other positions are within the scope of the present disclosure.

The inflatable balloon 16 includes an optional gauze material 44 that surrounds the inflatable balloon 16, or at least a portion thereof. The gauze material 44 may be configured to provide enhanced clotting ability. For example, the gauze material 44 may be a hemostatic-infused gauze and function as a hemostatic sheath. In some embodiments, a hemostatic powder dispersal mechanism may be utilized to further enhance the mitigation of bleeding from the wound 40, shown in FIG. 3, by applying hemostatic powder 46 to the wound 40, shown in FIG. 3, before inflation of the inflatable balloon 16. For example, the hemostatic powder 46 may be deposited on the inflatable balloon 16, i.e., wound blocking contents, so that the hemostatic powder is dispersed into the wound 40 when the inflatable balloon 16 is expelled from the outer storage container housing 12. The hemostatic powder 46 may be sprayed into the wound 40 cavity, shown in FIG. 3, by pressing the hemostatic powder 46 through a mesh during expulsion. The un-inflated balloon 16 is then pressed into the wound 40 by the continued motion of the piston 24 and the balloon 16 begins to inflate in the wound 40 once the piston 24 reaches the end of its travel at the piston stop 26 or substantially proximate thereto, as discussed above. The inflatable balloon 16 is inflated inside the hemostatic sheath (if equipped) and inflates to fill the wound cavity 40, thereby applying pressure to the entire area contacted by the inflatable balloon 16. In this embodiment, the piston stop 26 is arranged at the distal end 36 of the device 10.

In some embodiments, the wound blocking content(s) 16 comprises gauze, antibiotic agents, hemostatic material and/or powder for wound treatment, or any combination thereof in conjunction with the inflatable balloon, or used independently. Additionally, while the activator 28 is shown in the form of a button in FIGS. 1 and 2, other activation mechanisms are within the scope of the present disclosure. For example, and without limitation, the activator 28 may be a switch, diaphragm, knob, slider or electronic assembly configured to activate the bleeding control device 10 following an input from a user.

Referring to FIG. 3, a schematic illustration of a variant embodiment of the bleeding control device 10 of FIG. 1 is shown in a deployed state in a wound 40 of a patient 42. This embodiment differs from the embodiment of FIG. 1 in that the piston stop 26 is arranged at the distal end 36 of the device 10 instead of at an intermediate position as shown in FIG. 1. The distal end 36 of the outer storage container housing 12 is placed directly into the wound 40 of the patient 42 or substantially proximate thereto by a user, which may be any person operating the bleeding control device 10, including the patient in some circumstances. Then, the user actuates the activator 28. As discussed above, in this embodiment, the activator 28 is actuated by pressing the activator 28 into the interior of the outer storage container housing 12 at the proximate end 38 towards the compressed gas canister 14. This presses the compressed gas canister 14 against the piercing end 22 of the gas supply line 18, shown in FIG. 1, thereby piercing the compressed gas canister 14 and causing pressurized gas to flow into the outer storage container housing 12. The pressurized gas flows throughout the outer storage container housing 12, both outside the gas supply line 18 and within the gas supply line 18. The pressurized gas outside of the gas supply line 18 causes the piston 24 to move toward the distal end 36 and causes the inflatable balloon 16 (the wound blocking content(s)) to exit the outer storage container housing 12 at the distal end 36 and move into the wound 40 of the patient 42. When the piston 24 finishes its travel and/or reaches the piston stop 26, the pressurized gas inside the gas supply line 18 inflates the inflatable balloon 16 to fill the wound 40.

The pressure of the gas delivered from the compressed gas canister 14 is fed into the regulator 30, which at least initially drives the piston 24 to expel some or all of the wound blocking contents 16, including the inflatable balloon, from outer storage container housing 12 and into the wound 40. The pressure driving the piston 24 may, at least initially, be higher than the pressure inflating the inflatable balloon 16 to ensure the inflatable balloon (or wound blocking contents) 16 are ejected from the outer storage container housing 12. As the inflatable balloon 16 inflates, the inflatable balloon 16 fills the cavity of the wound 40. The regulator 30 can be adjusted through the adjustable control 32 to increase or decrease the pressure in the inflatable balloon 16 if the desired outcome is not being achieved. For example, the pressure may be increased if the wound blocking contents 16 is not sufficiently sealing the wound 40 or may be decreased if it appears that the inflatable balloon is overinflated relative to the cavity of the wound 40. The regulator 30 may have a plurality of different discrete pressure level settings of inflation pressure and may initially be set to its lowest pressure level setting and then increased depending on the pressure required to stop bleeding or a desired pressure is reached. The regulator 30 may also serve to keep the inflatable balloon 16 at a given or steady inflation level once inflated so as to not over-pressurize or under-pressurize the inflatable balloon 16. If the pressure is not sufficient to staunch the bleeding, a user may manually select to increase the regulator 30 setting through the adjustable control 32 to the next pressure level setting to further pressurize the balloon 16 to achieve the desired result.

While the compressed gas canister 14 has been described herein as being filled with gas, other materials or substances configured to be stored under pressure are within the scope of the present disclosure. For example, and without limitation, the compressed gas canister 14 may be charged with carbon dioxide, oxygen, nitrogen, argon, and/or water. While the gas supply line 18 is shown as a single piece rigid tube, it is within the scope of the present disclosure for the gas supply line 18 to be a plurality of rigid tubes (i.e. multi-piece), or a flexible tubing, or any combination thereof. For example, the gas supply line 18 could be a single rigid tube connected to flexible tubing(s) or a plurality of rigid tubes connected to flexible tubing(s).

Figure 4:
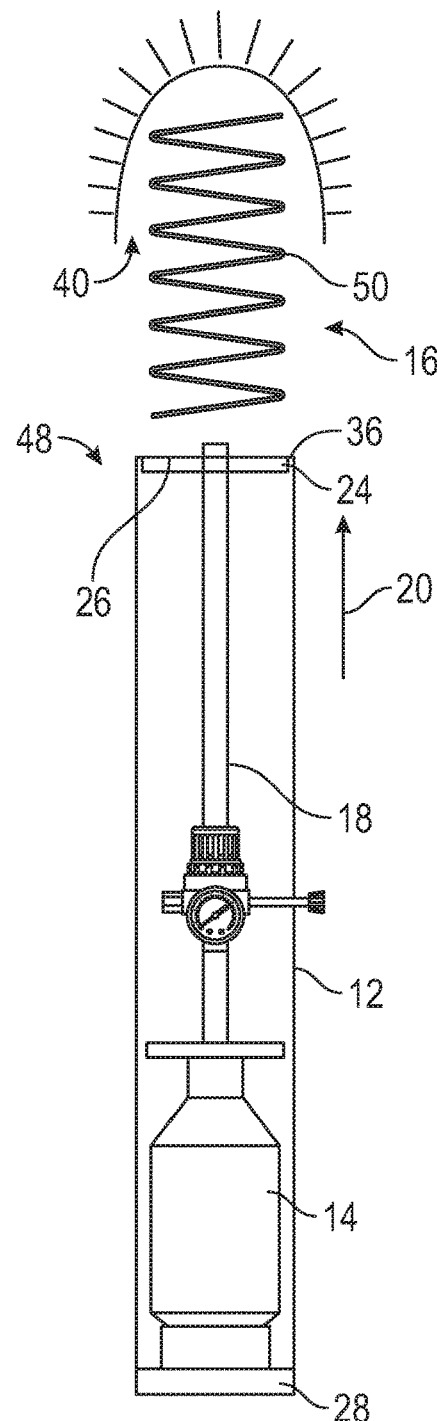
FIG. 4 is an illustration of a bleeding control device in a deployed state in accordance with the present disclosure.

Referring to FIG. 4, a bleeding control device 48 according to another embodiment comprising an alternative wound blocking contents 16 is shown in a deployed state. Elements with like reference numerals to elements discussed above in connection with FIGS. 1-3 are the same and will not be discussed in further detail. In this second embodiment, the wound blocking contents 16 are in the form of packed gauze 50. The piston 24 forces the packed gauze 50 out of the outer storage container housing 12 into or around the wound 40. As the gauze 50 exits the outer storage container housing 12 at the distal end 36, the gauze 50 spreads out to cover the wound 40, thereby controlling and/or blocking bleeding from the wound 40. As with the wound blocking contents discussed above, the gauze 50 may be embedded with a hemostatic agent or powder to provide a faster alternative than manual wound packing while providing a similar result.

Figure 5:
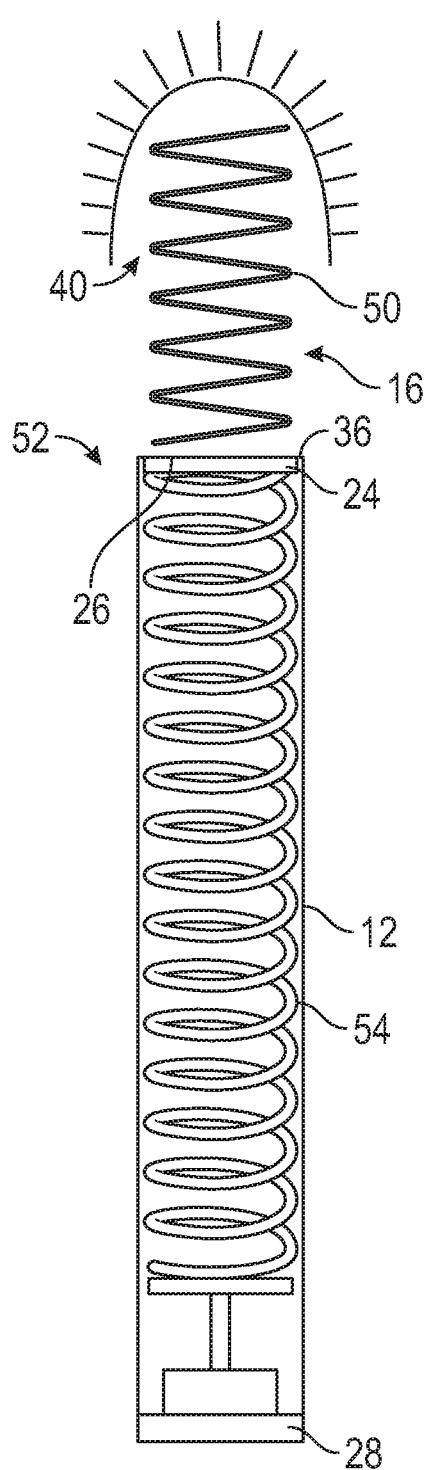
FIG. 5 is an illustration of a bleeding control device in a deployed state in accordance with the present disclosure.

Referring to FIG. 5, a bleeding control device 52 is shown in accordance with another embodiment of the present disclosure. Elements with like reference numerals to elements discussed above in connection with FIGS. 1-4 are the same and will not be discussed in further detail. In this third embodiment, the bleeding control device 52 includes a spring deployment system for deploying the wound blocking contents 16 instead of the compressed gas delivery system discussed above. The spring deployment system comprises a spring 54, or other similar resilient member, that is configured to drive the wound blocking contents 16 from the distal end 36 of the outer storage container housing 12 when activated by the activator 28. The spring 54 is in a compressed state when the device 52 is in a non-deployed state, and expands to a non-compressed state (or less compressed state) when the device 52 is activated by the activator 28 to deploy the wound blocking content(s) 16 as the device 52 transitions to a deployed state. The choice between the spring deployment system and the compressed gas delivery system may be based on the deployment and/or reliability characteristics desired in the resulting bleeding control device.

Figure 6:
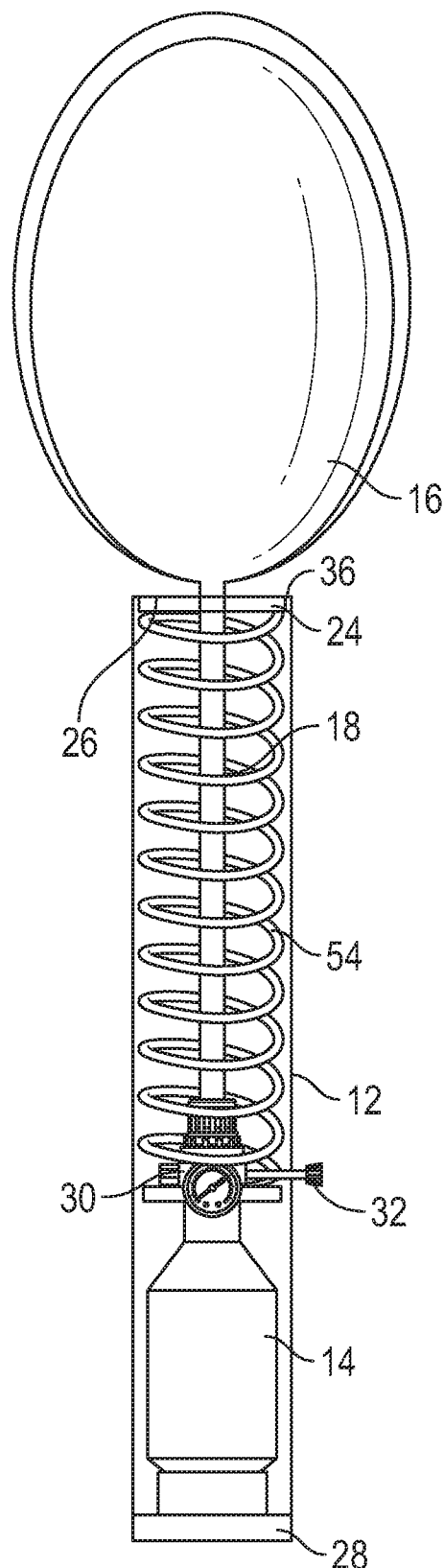
FIG. 6 is an illustration of a bleeding control device in a deployed state in accordance with the present disclosure.

Referring to FIG. 6, a bleeding control device 56 is shown in accordance with another embodiment of the present disclosure. Elements with like reference numerals to elements discussed above in connection with FIGS. 1-5 are the same and will not be discussed in further detail. The bleeding control device 56 includes the spring deployment system discussed above in connection with FIG. 5 to deploy the wound blocking contents 16 from the outer storage container housing 12. In the embodiment shown in FIG. 6, the wound blocking contents 16 is the inflatable balloon 16 as in FIGS. 1-3. In this embodiment, the compressed gas canister 14 inflates the inflatable balloon 16 only when the bleeding control device 56 is activated, but does not provide the driving force for driving the piston 24 to force the wound blocking contents 16 from the distal end 36 of the outer storage container housing 12 of the bleeding control device 56. Actuation of the activator 28 may simultaneously (or substantially simultaneously) activate both the spring 54 of the spring deployment system and the compressed gas canister 14. Alternatively, the bleeding control device 56 may include separate activators 28 for the spring 54 and compressed gas canister 14. As discussed in the embodiments above, once the inflatable balloon 16 is deployed, a regulator 30 may control pressure from the compressed gas canister 14 to inflate the inflatable balloon 16 to the desired pressure and/or to maintain the pressure, for example, within predetermined upper and lower pressure limits.

Figure 7A:
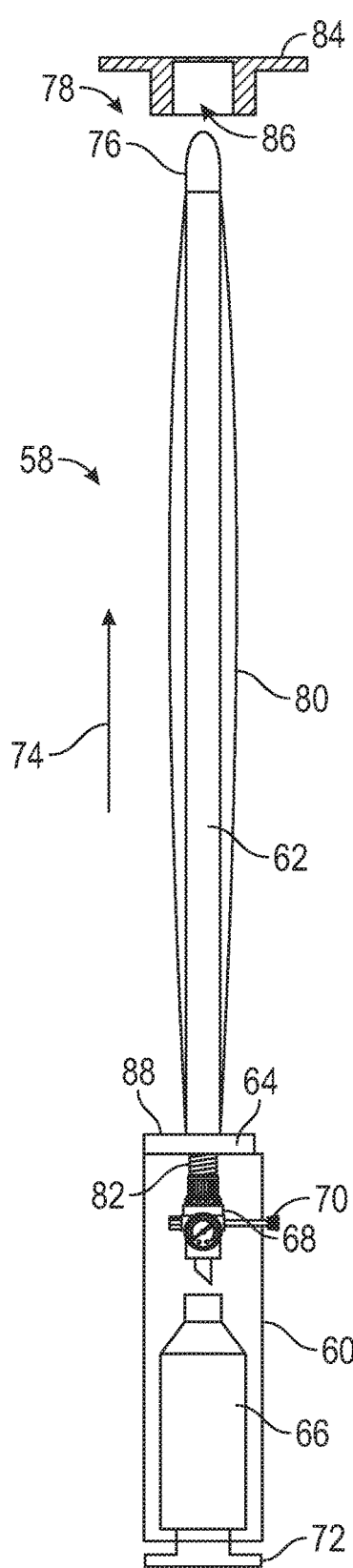
FIG. 7A is an illustration of a bleeding control device in a non-deployed state in accordance with the present disclosure.
Figure 7B:
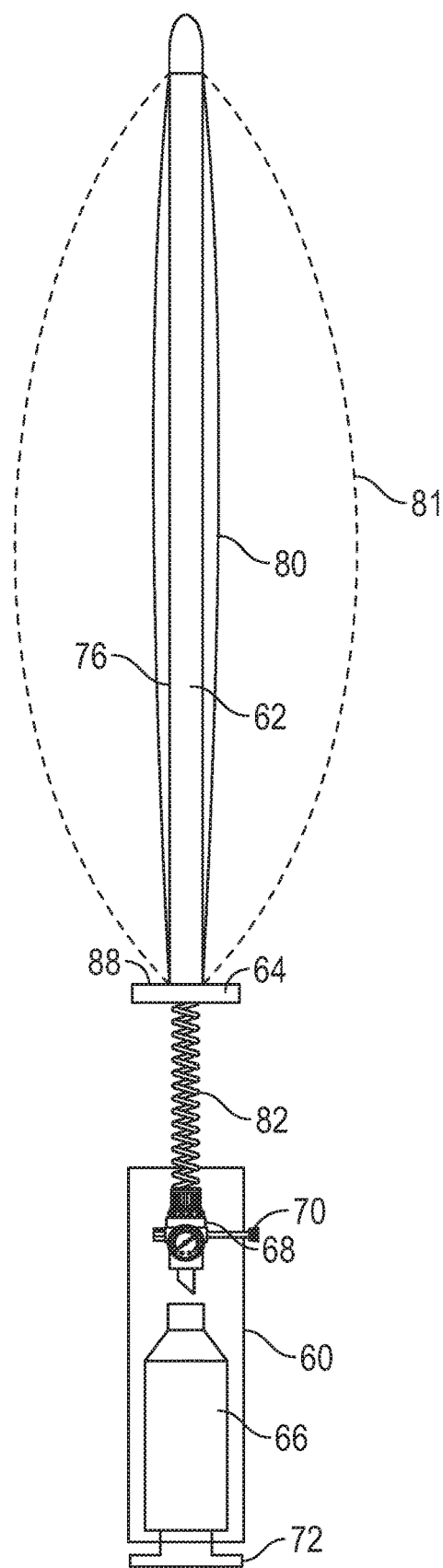
FIG. 7B is an illustration of the bleeding control device of FIG. 7A with the detachable base detached from the canister housing in accordance with the present disclosure.

Referring to FIGS. 7A and 7B, a bleeding control device 58 is shown in accordance with an embodiment of the present disclosure. The device 58 comprises a canister housing 60 connected to a rigid tube 62 through an optional detachable base 64. The detachable base 64 is configured to detach from the canister housing 60. The canister housing 60 includes a compressed gas canister 66 having an optional regulator 68 and adjustable control 70. The compressed gas canister 66 is configured to be activated by an activator 72. The rigid tube 62 extends in a longitudinal direction 74 and includes a pliable tip 76 at a distal end 78 within an inflatable balloon 80. The compressed gas canister 66 is fluidly connected to the inflatable balloon 80 through flexible tubing 82 and is configured to inflate the inflatable balloon 80 when activated by the activator 72. While the tube 62 is described as being a rigid tube, virtually all degrees of rigidity of tubes are within the scope of the present disclosure. Further, the rigid tube 62 may be hollow or solid. Additionally, the bleeding control device 58 may optionally include a cap and/or sleeve (not shown) configured to cover the balloon 80 and rigid tube 62 when the bleeding control device 58 is in the non-deployed state to protect the balloon 80 and/or rigid tube 62 from damage and/or contamination before insertion into a wound. In FIG. 7B, the bleeding control device 58 is shown with the detachable base 64 detached from the canister housing 60 and with broken lines 81 indicating a shape and size of the inflatable balloon 80 when under pressure in an inflated state. Even when detached, the pressure of the inflatable balloon 80 may be controlled via adjustment of the adjustable control 70, thereby controlling the pressure in the inflatable balloon 80 through the flexible tubing 82. While the broken lines 81 show a particular shape and size of the balloon 80 in the inflated state, it is within the scope of the present disclosure for the balloon 80 to be configured to inflate to a different shape and/or size as desired.

In operation, the optional cap (not shown) is removed from the device 58 before use, if so equipped. The bleeding control device 58 may then be inserted into a wound, distal end 78 first, through an optional guide/limiter 84 that prevents the balloon 80 from further widening the entry point of the wound. The optional guide/limiter 84 defines a through-cavity 86 that is sized to receive the balloon 80 and rigid tube 62 when the inflatable balloon 80 is not inflated. The bleeding control device 58 may be inserted to a desired depth and/or until the user inserting the device 58 feels a sufficient amount of resistance. For example, the bleeding control device 58 may be inserted until met with resistance from a bullet (or other foreign object) where the bullet (or other foreign object) is still in the patient, or may be inserted to a desired depth or until met with resistance from the bottom of a wound cavity when no bullet or foreign object is present in the patient, such as for a stab or puncture injury. The balloon 80 may optionally be marked with longitudinal measurements in the longitudinal direction 74 to indicate the depth of the wound cavity when inserted into a patient. The maximum pressure may be limited to avoid causing further damage. Once the bleeding control device 58 is positioned in the wound, the activator 72 is actuated to activate the compressed gas canister 66, thereby causing pressurized gas to flow through the flexible tubing 82 and into the inflatable balloon 80 to inflate the inflatable balloon 80. The inflation of the inflatable balloon 80 applies pressure to the wound to mitigate bleeding until the patient can receive appropriate and more thorough medical care.

Once the inflatable balloon 80 has been inflated in the wound cavity, the canister housing 60 may be detached via the detachable base 64 and may be positioned away from the wound. For example, the canister housing 60 may be arranged flat against the body and secured to the patient or the patient's clothing by a hook and loop type fastener, adhesive, tape, or any similar fastening mechanism. The rigid tube 62 could then also be removed, if desired, with a gasket material 88 preventing gas from escaping from the balloon 80 through the opening where the rigid tube 62 was arranged. The rod 62 and tubing 82 may be offset so the removal of one does not affect the other. The rigid tube 62 can also be removed at any time after inflation without the base 64 being detached from the body 60. The regulator 68 may be configured for maintaining the desired pressure level within the balloon 80 and, therefore, would replenish gas lost due to an imperfect seal by the gasket material or gland 88, or any unintended perforations of the balloon if necessary. Once the gas cylinder is relocated against the body of the patient, additional bandages may be wrapped around the wound to provide additional pressure and/or clotting assistance.

Advantageously, the device 58 having the detachable base 64 being configured to detach from the canister housing 60 allows for the canister housing 60 to become detached such that the canister housing 60 may be laid down and secured to the patient's body, thereby reducing length of the device 58 protruding from the patient in the longitudinal direction 74. This reduction in length reduces the potential for interference by the device 58 with first responders and/or medical professionals while attending to the needs of the patient. The reduction in length may decrease the likelihood of the balloon 80 being jostled or dislodged by contact with a person or object. In some embodiments, for an even greater reduction in length and reduction of potential interference, the rigid tube 62 and/or gas supply line 82 is optionally removable from the inflatable balloon 80. The inflatable balloon 80 may include the gasket 88 (or self-sealing grommet or valve) to prevent loss of pressure of the inflatable balloon 80 after removal of the rigid tube 62 and/or gas supply line 82.

Advantageously, the device 58 allows for mitigating the bleeding of wounds having relatively narrow entry points due to the configuration of the inflatable balloon 80 around the rigid tube 62. For example, the device 58 may be configured to address bleeding stemming from a wound caused by a common military rifle caliber, such as 5.56 mm or 7.62 mm, which may have a potentially more narrow entry point opening compared to handgun wound entry point openings. However, since the inflatable balloon 80 inflates to fill the wound cavity, this embodiment is also applicable for use with larger wounds and/or larger entry point openings.

In some embodiments, the device 58 is configured such that the inflatable balloon 80 inflates at different rates and/or inflates to different widths. For example, the balloon 80 may be configured with a progressive thickness so that a first portion of the balloon 80 near the distal end 78 inflates before a second portion of the balloon 80 further from the distal end 78 than the first portion in the longitudinal direction 74 (e.g. a second portion nearest the canister housing 60), and/or inflates to a different size and/or shape in order to provide a different applied pressures at different regions of the balloon 80 in the longitudinal direction 74. A balloon 80 configured in this manner may control bleeding by first filling a distal gap in an exit wound opening, or in the case of a wound without an exit, the wound portion furthest from the entry wound, which may be larger than an entry wound opening to avoid opening the entry wound further and/or by applying more/less pressure at one portion of the wound relative to another portion of the wound because of the predetermined shape of the balloon 80.

Figure 8:
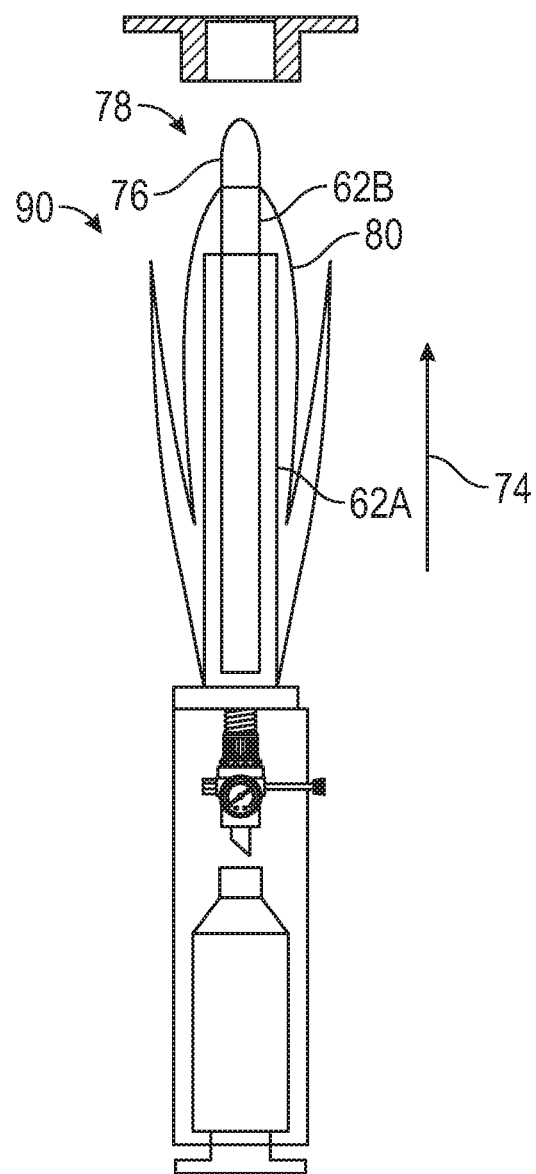
FIG. 8 is an illustration of a bleeding control device in a non-deployed state in accordance with the present disclosure.

Referring to FIG. 8, a bleeding control device 90 is shown in accordance with the present disclosure. The device 90 is similar in structure and use to the device 58 of FIG. 7. Elements with like reference numerals to elements discussed above in connection with FIGS. 1-7 are the same and will not be discussed in further detail. In this embodiment, there is a multi-piece tube or rod structure comprising an outer tube 62A and an inner tube (or rod) 62B. The inner tube 62B includes a pliable tip 76 at a distal end 78. The difference in use is that once the cap was removed the top of the balloon 80 may be loosely tethered to the cap to extend the inner tube 62B to full length or the user could manually extend the balloon 80 (preferably with a gloved hand) by withdrawing the inner tube 62B from the outer tube 62A in a longitudinal direction 74. The tube may have a protrusion that locks the tube (or rod) 62A in place to prevent the tube (or rod) 62A from being collapsed once extended. The remainder of the use is the same as the description above. Advantageously, this embodiment may provide a more compact package to facilitate the carrying and/or storage of the device 90 when not in use. In some embodiments, the length of the outer tube 62A and inner tube (or rod) 62B is for instance, 6-8 inches in length in the longitudinal direction 74 when in the collapsed condition, but 12 inches in length when fully extended. However, other lengths (in both the collapsed and fully extended conditions) are within the scope of the present disclosure. For example, in the collapsed condition the length of the outer tube 62A and inner tube (or rod) 62B may be 4 inches in length in the longitudinal direction 74.

Advantageously, bleeding control devices in accordance with the present disclosure may comprise an inflatable balloon, gauze, a hemostatic material or powder for wound treatment, or any combination thereof. In some embodiments, a safety lockout may be provided to prevent accidental discharge. Additionally, all of the wound blocking contents described herein may advantageously include X-Ray contrast material such as a fine metal wire, metalized polyester film embedded in the balloon or other such devices configured to show up on an x-ray in order to alert medical staff to the balloon's or wound blocking contents' presence within the wound.

In use of the various bleeding control devices described herein, an end of the device being used is placed proximate to, or directly into, a wound opening and the actuator button is pressed or actuated. When the actuator button is actuated, the compressed gas canister, potentially filled with CO2, will either be pierced, or otherwise caused to open to direct gas flow within the outer storage container housing. The gas flow may be directed through a regulator that controls the gas flow pressure to drive a piston forward within the outer storage container housing to eject or expel the wound blocking contents out of the end of the device and into and/or around the wound cavity. If bleeding control is pursued quickly and correctly with the various bleeding control devices described herein, bleeding may be quickly controlled until more advanced care and treatment can be obtained.

According to the present disclosure, a bleeding control method comprises providing a bleeding control device, and activating the bleeding control device to deploy wound blocking content(s) contained within an outer storage container housing into a wound of a patient. In some embodiments, the wound blocking content(s) comprise an inflatable balloon, and the method further comprises inflating the inflatable balloon to a predetermined pressure or desired pressure while the inflatable balloon is inside the wound in order to apply sufficient pressure to the wound to stop or reduce bleeding.

In some embodiments, the compressed gas canister may be replaceable with a replacement cartridge compressed gas canister. In other embodiments, the compressed gas canister cannot be replaced and the bleeding control device is a single use device. Alternatively, the bleeding control device may include a compressed gas canister that cannot be replaced, but the compressed gas canister may have enough charge therein for several uses where the wound blocking contents are replaced. In some embodiments, the replacement cartridge compressed gas canister has a threaded portion allowing the compressed gas canister to thread directly with the regulator of the device.

In accordance with the present disclosure, different packaging options are available for the inflatable balloon being disposed within the outer storage container housing. For example, inflatable balloons with different inflation characteristics may be provided to conform to different wound types, such as deep narrow wounds, wide narrow wounds or wounds with distinctive entry wound openings. Moreover, the various bleeding control devices described herein may be configured so that a user can replace the inflatable balloons by attaching them to a gas nozzle in communication with the regulator so that the user can select an appropriate balloon for a specific wound. Any of the inflatable balloon size or shape configurations may be provided with hemostatic-infused gauze surrounding the balloon to encourage clotting by additional means than solely by pressure as discussed above. A powder dispersal mechanism, which could be a plastic mesh and packed powder positioned within the outer storage container housing before the balloon also may be used to spread a clotting agent or any other agent such as, but not limited to, antibacterial agents before applying pressure to the wound with the balloon.

All balloon variants of wound blocking contents in accordance with the present disclosure may make use of a regulator, which could be operated to increase or decrease pressure if the desired outcome is not being achieved. The balloon may have a short length of tubing that would allow the body of the device to be laid on top of the patient with the outer container of the device having hook fasteners (similar to the hook side of hook and loop fasteners) to stick to the clothing or bandages of the patient. The regulator may have a deflation setting or could be pierced by hospital staff once the patient arrives at a care facility in order to deflate the inflatable balloon for removal from the wound. All balloon variants may be configured to maintain an inflation and regulation source.

Additionally, in accordance with some embodiments of the present disclosure, z-folded gauze or other absorptive material may be injected into and/or around a wound cavity. The gauze could be packed within the outer storage container housing in a folded state, and unfold in or around the wound cavity once deployed. The gauze may also include an embedded hemostatic agent or powder to more quickly mitigate bleeding compared to traditional manual wound packing. If required, multiple devices may be utilized to complete wound packing and provide an expedited form for tending to a bleeding wound. Additionally, such devices may be used along side a traditional pressure bandage and manual pressure.

In some embodiments according to the present disclosure, a bleeding control device may be used to deploy a powder to a wound. As disclosed herein, the powder could be deployed with additional wound blocking contents, such as a balloon or gauze packing. In the alternative, the storage container could be packed with powder and the pressing of the actuator button deploys a power to the wound cavity. The powder may be hemostatic or a mixture of hemostatic and antibiotic materials or the like.

In some embodiments according to the present disclosure, a bleeding control device may utilize a balloon or balloon sheath coated with a thin layer of antibacterial cream which may assist in insertion and direct application to the balloon areas of contact.

Advantageously, the present disclosure provides bleeding control devices that provide new, optimized and efficient approaches to covering and blocking a wound to control bleeding.

Although various features have been shown in different figures for simplicity, it should be readily apparent to one of skill in the art that various features may be combined without departing from the scope of the present disclosure.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A bleeding control device comprising:
an outer storage container housing;
a compressed spring arranged within the outer storage container housing;
wound blocking content arranged within the outer storage container housing; and
an activator configured to activate the compressed spring to deploy the wound blocking content from the outer storage container housing,
wherein the wound blocking content is configured to pack an open wound when deployed.

2. The bleeding control device according to claim 1, further comprising a compressed gas canister and a regulator, wherein the wound blocking content comprises an inflatable balloon, wherein the regulator is configured to regulate a pressure inside the inflatable balloon when the compressed gas canister is activated.

3. The bleeding control device according to claim 2, wherein the inflatable balloon is coated with an antibacterial cream.

4. The bleeding control device according to claim 2, further comprising an adjustable control connected to the regulator, wherein the adjustable control is selectively adjustable to vary the pressure inside the inflatable balloon when the compressed gas canister is activated.

5. The bleeding control device according to claim 4, wherein the inflatable balloon is coated with an antibacterial cream.

6. The bleeding control device according to claim 1, wherein the wound blocking content comprises packed gauze or other absorptive material.

7. The bleeding control device according to claim 1, wherein the wound blocking content comprises a hemostatic and/or antibiotic material.

8. The bleeding control device according to claim 1, further comprising a piston, wherein the compressed spring is configured to drive the piston to deploy the wound blocking content from the outer storage container housing when activated by the activator.

9. The bleeding control device according to claim 8, further comprising a stop configured to prevent the piston from moving beyond the stop in a longitudinal direction of the outer storage container housing.

10. The bleeding control device according to claim 1, further comprising a compressed gas canister, wherein the wound blocking content comprises an inflatable balloon.

11. The bleeding control device according to claim 10, further comprising a valve configured to determine an opening degree of the compressed gas canister.

12. A bleeding control device comprising:
an outer storage container housing;
a resilient member arranged within the outer storage container housing;
wound blocking content arranged within the outer storage container housing; and
an activator configured to activate the resilient member to deploy the wound blocking content from the outer storage container housing;
wherein the wound blocking content is configured to pack an open wound when deployed.

13. The bleeding control device according to claim 12, wherein the wound blocking content comprises packed gauze or other absorptive material.

14. The bleeding control device according to claim 12, further comprising a piston, wherein the compressed spring is configured to drive the piston to deploy the wound blocking content from the outer storage container housing when activated by the activator.

15. The bleeding control device according to claim 12, further comprising a stop configured to prevent the piston from moving beyond the stop in a longitudinal direction of the outer storage container housing.

* * * * *